United States Patent [19]

Jackson

[11] Patent Number: 5,439,801
[45] Date of Patent: Aug. 8, 1995

[54] TEST COMPOSITION FOR THE RAPID DETECTION OF HELICOBACTER PYLORI IN GASTRIC BIOPSY TISSUE

[75] Inventor: Frank W. Jackson, Mechanicsburg, Pa.

[73] Assignee: Chek-Med Systems, Inc., Camp Hill, Pa.

[21] Appl. No.: 195,954

[22] Filed: Feb. 14, 1994

[51] Int. Cl.$^6$ .......................... G12Q 1/58; G01N 33/48
[52] U.S. Cl. ........................................... 435/12; 435/1; 435/4; 435/10; 435/34; 436/63; 436/811
[58] Field of Search ...................... 435/12, 1, 4, 10, 34; 436/63, 811

[56] References Cited

U.S. PATENT DOCUMENTS

| | | | |
|---|---|---|---|
| 3,395,082 | 7/1968 | Mast | 195/103.5 |
| 3,461,036 | 8/1969 | Horcil | 435/12 |
| 4,101,382 | 7/1978 | Chang | 195/103.5 |
| 4,282,316 | 8/1981 | Modrovich | 435/12 |
| 4,748,113 | 5/1988 | Marshall | 435/12 |
| 5,258,178 | 11/1993 | Cordle et al. | 424/85.8 |
| 5,260,057 | 11/1993 | Cordle et al. | 424/85.8 |
| 5,304,540 | 4/1994 | Blackburn et al. | 514/2 |
| 5,314,804 | 5/1994 | Boguslaski et al. | 435/12 |

OTHER PUBLICATIONS

*Helicobacter pylori in Peptic Ulceration and Gastritis* Barry J. Marshall. Richard W. McCallum & Richard L. Guerraut, Blackwell Scientific Publication, Boston, Mass., USA, Chapters 4, 7 and 12.
"Marshall's Hunch", *The New Yorker Magazine*, pp. 64–72 Sep. 20, 1993.
"The Doctor Who Wouldn't Accept No", *Readers Digest Magazine*, pp. 120–124, Oct., 1993.
*Annals of Internal Medicine*, David Y. Graham, 1192; 116 No. 9.
Difco Manual, 9th Ed., Difco Laboratories, Detroit, Mich., 1952.
*Helicobacter pylori*, "Urease and Purification of its Subunits", D. G. Evans, Jr., S. S. Kirkpatrick and D. Y. Graham, 10:15–2G.
"Bacterium Causes Most Peptic Ulcers", Jerry E. Bishop, *The Wall Street Journal*, Feb. 10, 1994.

Primary Examiner—Michael G. Wityshyn
Assistant Examiner—Abdel A. Mohamed
Attorney, Agent, or Firm—Eugene Chovanes

[57] ABSTRACT

An improved test composition for the diagnosis of gastric disease by detecting the presence of urease associated with *H. pylori* in a biopsy specimen is described in which the hydrolysis of urea by urease is detected by a combination of at least two dye indicators showing a color change and a positive result at an acid pH, in which the positive color is distinctive from the color of the biopsy specimen, and in which most positive results occur in 2–10 minutes and all occur in no more than 4 hours. Specific compositions are disclosed.

10 Claims, No Drawings

TEST COMPOSITION FOR THE RAPID DETECTION OF HELICOBACTER PYLORI IN GASTRIC BIOPSY TISSUE

The present invention relates to an improved test composition for the diagnosis of gastrointestinal disorders. The new test composition is particularly useful for the diagnosis of peptic ulcers, including both gastric and duodenal ulcers, by detecting the urease enzyme associated with the bacteria *Helicobacter pylori* in endoscopically obtained biopsy specimens. The test is not intended for in vivo use but only for in vitro diagnosis.

BACKGROUND AND PRIOR ART

Peptic ulcers, once thought to result from stress, or excess acidity, or a reduction of the mucosal defense factors in the stomach, are now in a majority of cases, considered to be the result of bacterial infection by *Helicobacter pylori*. The mounting evidence to this effect is well documented in *Helicobacter pylori in Peptic Ulceration and Gastritis*, edited by Barry J. Marshall, Richard W. McCallum and Richard L. Guerraut, Blackwell Scientific Publications, Boston, U.S.A. Pertinent Chapters in this work include Chapter four, The Epidemiology of *Helicobacter pylori* Infection by D. N. Taylor and M. J. Blaser; Chapter seven, Laboratory Diagnosis and Handling of *Helicobacter pylori*, by T. U. Westblom; and Chapter twelve, Practical Diagnosis of *Helicobacter pylori* by B. J. Marshall. The history of the discovery *H. pylori* and its association with gastro intestinal disease is extensively described in "Marshall's Hunch," *The New Yorker* magazine, pages 64–72, Sep. 20, 1993 and "The Doctor Who Wouldn't Accept No," *Reader's Digest* magazine, pages 120–124, October 1993.

The effect of treatment of *Helicobacter pylori* Infection on long term recurrence of Gastric or Duodenal Ulcer is described by David Y. Graham et al in *Annals of Internal Medicine* 1992; 116: No 9.

*Helicobacter pylori* has now been shown to be the causative agent for most instances of chronic gastritis (1). See the bibliography below. And, it is now known that, in the absence of aspirin, non-steroidal anti-inflammatory drugs or hypersecretory states, this bacteria is directly implicated in the production of peptic ulcer diseases such as duodenal and benign gastric ulcers (2). And there is now epidemiological data correlating the presence of the *H. pylori* with gastric cancer (3). The eradication of *H. pylori* gastritis by antibiotics has been shown to cure peptic ulcers and prevent recurrence (4,5).

It having been seen that the bacteria *H. pylori*, is present in endoscopically obtained gastric biopsy specimens from both gastric and duodenal ulcer patients and it being known that the enzyme urease is always associated with that bacteria, the concept of diagnosing the presence of such ulcers by testing biopsy specimens for urease suggested itself. Chemical tests for urease were already known in the art. In one such test a urea-containing broth provides a positive urease reaction (hydrolysis of urea) urea+$H_2O$ urease→$NH_3$+$CO_2$ as indicated by a change in color of the indicator Bacto phenol red from yellow (pH 6.8) to red to cerise at pH 8.1 or more alkaline due to the production of ammonia and/or ammonium carbonate by the urea-urease reaction. See the Difco Manual, 9th edition, Difco Laboratories, Detroit, Mich., (1953). The urea broth described in the Difco Manual was apparently used by B. J. Marshall in the work described in the Rapid Diagnosis of *Campylobacteria* Associated with Gastritis, *The Lancet*, Jun. 22, 1985.

This type of urease test has come into commercial and clinical use. In the United States a commercial test product is marketed under the trademark "Clotest." This product is described in U.S. Pat. No. 4,748,113 issued to Barry J. Marshall, on May 31, 1988.

Inasmuch as this test is based upon the reaction of the urease enzyme with urea it will be apparent to any chemist that this reaction can be used to detect either urea or urease, whichever is present in the material to be tested, by the addition of the other material in a test solution. The course of the reaction can be followed by the use of known dye indicators which change color with the changing pH of the reaction mixture as the reaction proceeds. Therefore, references to the detection of urea in the blood or elsewhere are also pertinent. Such references include Mast U.S. Pat. No. 3,395,082 issued Jul. 30, 1968 for a test for urea in aqueous fluids; Chang U.S. Pat. No. 4,101,382 issued Jul. 18, 1978 for a reagent for the determination of urea in biological fluids; and Modrovich U.S. Pat. No. 4,282,316 issued Aug. 4, 1981 for stabilized enzymatic solutions for determining urea.

The detection of preformed urease for the diagnosis of gastrointestinal disorders by the use of water, urea, a bactericide and a pH indicator, is described in by B. J. Marshall Derwent Publication C-86-141647 (1986). The use of urease to determine urea is also described in Derwent Publication C84-128710 (1985). A non-aqueous analytical unit for urease determination, consisting of urea, a buffer for pH 5 to 7.5 and pH indicator, is described in Derwent Publication C90-068529 (1990).

The test composition marketed under the trademark "Clotest" as disclosed in Marshall U.S. Pat. No. 4,748,113 has the following composition:

| | |
|---|---|
| a) Urea | 10–40 g/liter |
| b) A bactericide | 1–5 g/liter |
| c) A dye indicator having A pKa of from about 6.5–8.5- | effective amount |
| d) Water Wherein the composition has a pH of from about 5.0–6.5 and in which the pH is at least about one pH unit lower than the pKa of the indicator. | To make 1.0 liter |

The composition of the Marshall patent uses phenol red alone as the dye indicator.

The method of the Marshall patent is initiated by obtaining a sample of gastric material from the patient by endoscopic biopsy according to procedures well known in the art. The biopsy specimen is then contacted with the test composition set forth above. The test composition is said to be used in liquid form as a rule but may also be gelled. The change in color of the phenol red from yellow at the initial pH (about 5.0–6.5) to red at a pH of about 6.8–9 by the formation of ammonia and/or ammonium carbonate in the hydrolysis reaction, indicates the presence of urease and the *Helicobacter pylori* bacteria to be identified in the biopsy specimen.

While the test described by Marshall has proven to be highly useful, it has been recognized that it could be improved in certain respects. In the Marshal urease test gastric mucosal biopsy containing *H. pylori* is placed in solution or an agar gel containing urea, an indicator phenol red, and buffers. The urease in *H. pylori* converts the urea to ammonia which raises the pH and turns the agar color from a yellow to red, indicating a positive test. According to the package insert in the main commercial phenol red test available (called CLOtest ®), it is recommended that the test be incubated at 30°–40° C. for three hours and that it may take up to 24 hours to develop a positive test. This test relies on the passive diffusion of urease from the cell wall of the bacterium into the agar gel testing solution. Moreover, operating as it does at a pH above 6.5, the test may give a positive result with bacteria other than *H. Pylori* and thus is not entirely specific for *Helicobacter pylori*. Specifically, *proteus*, Pseudomonas and *E. Coli* species may cause a color change at this level and give a false positive test.

It was apparent therefore that a need has existed in the art for a highly specific test for *Helicobacter pylori* which would enable diagnosis of a gastrointestinal disorder during a patient's single visit of normal duration to a physician or clinic.

SUMMARY OF THE INVENTION

The present invention resides in an improved test composition for detecting the presence of *Helicobacter pylori* in a biopsy specimen for the purpose of diagnosing gastrointestinal disorders. Major improvements in the new composition inter alia reside in the improved specificity of the test for *H. pylori*; a color change not masked by the color of the biopsy specimen and which gives an indication of the degree of infection; and increased rapidity of the test permitting diagnosis during an initial patient visit.

The preferred new test composition is in the form of an aqueous gel containing:

| | |
|---|---|
| Urea | about 1% |
| Agar | about 1% |
| N-octyl glucose (pyranoside) (NOG) | about 1% |
| $NaH_2PO_4$ | 1.5 to 3.5 mM |
| Dye stock | 25% |
| Preservative agent | about 0.2% |
| Deionized water | remainder |
| | 100% |

The dye stock contains:

| | |
|---|---|
| Methyl red | 1% |
| Bromthymol blue | 0.1% |
| Deionized water | |

The preservative agent contains:

| | |
|---|---|
| Methyl paraben | 0.18% |
| Propyl paraben | 0.02% | all by weight of the total test composition in deionized water.

The preferred compositions as set forth above and below have a pH of about 5.2 to 5.3 at 55° C. Other useful compositions may have an initial pH in the range from about 4.9 to about 5.8.

The proportions of the various ingredients may vary as follows:

Urea from about 0.5 to about 2.0%; agar from about 0.4 to about 1.4%; N-octyl glucose (NOG) from about 0.2 to about 1.2%; monobasic sodium phosphate from about 1.5 mM to about 3.5 mM; methyl red from about 0.05 to about 0.40%; bromthymol blue from about 0.005 to about 0.040%; preservative agent, quantum sufficient, about 0.01 to about 0.2% total e.g., a preferred preservative agent being a combination of about 0.18% methyl paraben and about 0.02% propyl paraben; water>96% to make up to 100% of the composition; all percentages being by weight of the total composition.

Dye indicators other than those named above as preferred may be used in suitable amounts. Suitable compositions of dye indicators may include: bromocresol purple with bromocresol green, or bromocresol green with alizarin red 8 and, of course, with phenol red. Bromocresol purple is yellow at pH 5.2 and purple at pH 6.8 and therefore, could be the basis for various useful dye combinations. A useful three dye combination would be composed of e.g 0.133% methyl red, 0.133% bromthymol blue and 0.133% bromocresol purple.

The preservative agents methyl paraben and propyl paraben are well known in the art as food preservatives effective against bacteria, yeast and molds. Their use is restricted to up to about 0.1% in foods. These preservatives are most effective at acidic and neutral pH values. They are of limited solubility in water but this is overcome by using them in combination, such as methyl paraben and propyl paraben as above and as suggested in Antimicrobial Preservatives In Pharmaceuticals, p. 701, (please supply reference).

The monobasic sodium phosphate is not used as a buffer but is employed to provide the composition with the desired initial pH level of about 5.3 in the range from about 4.9 to 5.8. The absence of buffers in the new test compositions permits the pH to change more quickly. The color reaction, therefore, is often available for reading when the patient is recovering from endoscopy. Indeed, over 95% of all tests turn positive within 20 minutes, an occasional test may take as much as one hour, but all are positive within 4 hours. Therefore, there is no need to wait for 24 hours to be sure of a final result as with previously available test compositions.

The N-octyl glucose, a cell wall detergent, is employed to aid in freeing the urease enzyme from the biopsy specimen as will be explained further below.

The test composition is in the form of a soft gel which is capable of receiving the biopsy specimen and intimately contacting it in order to ensure as rapid interreaction as possible.

DETAILED DESCRIPTION OF THE INVENTION

The new test composition is formulated by mixing stock solutions prepared as follows:

1. Stock Solutions of Dyes.
   A. 1.0% methyl red (ICN catalog #151676) in distilled water
   B. 1.0% bromthymol blue (ICN catalog #150524) in distilled water
   Procedure:
   (1) Prepare 1:10 dilution of bromthymol blue by mixing 1 part of the 1% solution with 9 parts distilled water
   (2) Prepare a dye mixture consisting of equal parts of 1% methyl red solution and the 0.1% bromthymol blue 2. Other reagent stock solutions—all prepared in distilled or deionized water
   A. 8.0% NOG (N-octyl-glucose), (Sigma)
   B. 0.25M monobasic sodium phosphate
   C. 10.0% urea
   D. 2.0% Bacto agar (DIFCO)
3. To prepare final reagent mixture:
   A. Autoclave 2% agar solution (121° C. for 15 minutes minimum at −15 lb. pressure) then keep in 55° C. water bath until it is used
   B. Prepare 2× (double concentration) of following mixture:
      5.3 ml of the dye stock solution
      2.5 ml of 8% NOG
      0.2 ml of monobasic sodium phosphate solution
      2.0 ml of 10% urea solution
      Then filter-sterilize with 2 micron filter and mix with equal volume of the hot, autoclaved agar; dispense while liquid (45°–50° C.) Example, above mixture (10 ml)+10 ml agar yields 20 ml final reagent solution which is then used at 200 microliters per "unit" test.
4. Final concentration of reagents in the preferred rapid urease test composition:
   A. Methyl red: 0.1326% (3.77-fold dilution of 0.5% solution) Bromthymol blue: 0.0133% (3.77-fold dilution of 0.05% solution)
   B. 1% NOG
   C. 2.5 mM Monobasic sodium phosphate
   D. 1% Urea
   E. 1% Agar
   F. 0.2% Preservative (0.18% methyl paraben and 0.02% propyl paraben)
5. Final pH of rapid urease test reagent: pH 5.3 (color="peach")

An important advantage of the new test composition resides in the use of the combination of dye indicators, as opposed to a single dye indicator, which provides a wide spectrum of colors depending upon the concentration of H. pylori infection and the resulting change in pH.

The colors of the dye spectrum for varying pH are as follows:

| pH | Color Spectrum (Lighter Color with Smaller Volume!) |
|---|---|
| | Initial |
| 5.3 | dark peach |
| 5.4 | darker peach |
| | Negative for H. pylori |
| 5.6 | yellow-brown |
| 5.8 | greenish-yellow |
| 6.0 | light green |
| | Positive for H. pylori |
| 6.2 | dark green |
| 6.4 | darker green |
| 6.6 | emerald green |
| 6.8 | darker emerald green |
| 7.0 | aqua blue (light blue) |
| 7.2 | medium aqua blue |
| 7.4 | dark aqua blue |
| 7.6 | dark blue |
| 7.8 | dark "ink" blue |

The preferred test composition has an initial pH of about 5.3 and is peach to yellow brown in color. At a pH of about 6.0 the test solution becomes light green which is also considered to be a negative or indeterminant. A positive test for H. pylori occurs when the test solution turns dark green at a pH of about 6.2 or higher. This is in contrast to the commercially available test compositions which are still yellow (negative) at pH 6.2.

This scale may be further refined, if desired, by reading light green as negative; somewhat darker green as probably negative, dark green as weakly positive; darker green and emerald green or light blue as moderately positive; and darker aqua blue or dark blue as strongly positive. This color spread provides the physician with more quantitative and faster diagnostic information. A diagnosis can often be made within 2–10 minutes and so allow for effective treatment in a time effective manner. As noted above, over 95% of the tests, if positive, show the result within one hour and all within four hours; most tests showing a positive result in from 2–10 minutes.

Additionally, the colors green and blue are distinctly different from red and pink which are used in the phenol red test. Inasmuch as gastric biopsies are pinkish red, there may be difficulty in reading such tests in borderline cases when the indicator is phenol red alone.

While the optimal urease enzyme reaction for H. pylori takes place at alkaline pH, it is a very important advantage of the present invention that a positive reaction occurs on the acid side at a pH as low as 6.2. Of course, the pH may rise as high as about 7.8 in a highly positive test. This enhances the specificity of the improved test since other organisms such as Proteus, Pseudomonas and E. coli, which may be present in the biopsy specimen do not react in acid pH solutions. The test compositions of the prior art only produce positive results on the alkaline side above pH 7 and thus are less specific for H. pylori and may give false positives due to the presence of Proteus and other organisms. With the present test composition Proteus produces only a very light green test which is clearly a negative for H. pylori.

This wide spectrum of colors from peach through light green, green, light blue and dark blue, also provides a semi-quantification of the degree of infection which was not possible with the compositions of the prior art employing a single indicator such as phenol red which only turns from yellow to red.

The initial pH of the test solution at about 5.3 is achieved and maintained by the use of the monobasic sodium phosphate ($NaH_2PO_4$) which ensures that the test reaction is initiated in an acid pH where it is specific for H. pylori. The monobasic sodium phosphate does not act as a buffer, but merely lowers the pH to the desired initial level.

The purpose of the preservative agent is to ensure that the test solution is and remains sterile, i.e., that it does not contain any organism initially or grow any organism after inoculation with the biopsy test specimen, that would react with the test medium and produce a false positive result. In other words the preservative agent ensures that the test medium reacts solely with any H. pylori present in the biopsy specimen. As noted above, this is accomplished in the preferred test composition by the addition of 0.18% methyl paraben and 0.02% propyl paraben, a combination and concentration of preservatives known in the art to be effective to prevent the growth of bacteria in food and pharmaceutical compositions. As noted above, other preservatives known in the art may also be used.

A very important advantage of the new test composition resides in the use of NOG as a cell wall detergent. This agent is known in the art and to be effective as a cell wall detergent. Up to about 95% of the *H. pylori* urease is present in the cell wall of the biopsy specimen. The NOG, aiding in quickly releasing the urease enzyme from the biopsy specimen makes it more available for the reaction as has been confirmed by laboratory and clinical studies on patients. See characterization of *Helicobacter pylori* Urease and Purification of its Subunits by Evans, D. J. Jr., D. G. Kirkpatrick and S. S. Graham, D. Y. Microbiology Pathogenesis 1991, Vol. 10, pp. 15–26.

Agar softness permitting the biopsy test specimen to be readily embedded in the gelled test medium is an important improvement over the prior art and currently commercially available test products in which the gel is so firm that its rigid consistency makes it difficult for the technician to push the specimen into the test gel as it has a tendency to slide away. The softer gel of the present test composition not only more readily accepts the biopsy specimen when it is pushed in but also permits the gel to ooze completed around the biopsy specimen and make immediate intimate contact of the urease within the mucous membrane of the specimen with the test medium. This is a significant improvement over currently available test products in which the more rigid gels do not collapse around the specimen and tend to leave air pockets limiting contact between the specimen and test composition. It will be seen, therefore, that not only the use of NOG but the use of a softer gel facilitates contact and thus accelerates the test.

As noted briefly above, the initial pH of the test solution being about 4.9 to 5.6, preferably about 5.3 is well on the acidic side of the scale. While the optimal urease enzyme reaction of *H. pylori* is on the alkaline side of the scale, this reaction is still sufficiently effective under acidic conditions to be entirely satisfactory. Inasmuch as other bacteria such as Proteus and Pseudomonas react with urease only under alkaline conditions, the operation of the new test composition under acidic conditions precludes any false positive results due to the presence of bacteria other than *H. pylori*. Therefore, the new test is specific to the presence of *H. pylori*, and thus is far more reliable than the prior art tests for the diagnosis of gastric disease.

BIOPSY COLLECTION AND HANDLING

Patient Preparation

Antibiotics and bismuth, when used in suboptimal therapy, can suppress but not eliminate the *H. pylori* organism. Therefore, the patient should not have used these agents for several weeks prior to the test. Following inadequate therapy, the organism may regrow in a patchy manner and may not be detected by random biopsies. Ideally, the patient should not have received the proton pump inhibitor, omeprazole, as this drug has been shown to inhibit growth of the organism.

Evaluation and Preparation of the Test

A test kit containing the test composition in agar should be evaluated before the test is conducted. The agar should have a light peach color. A very light green color may indicate contamination and the subsequent result should be interpreted cautiously. An agar color of dark green or blue agar should be discarded.

Heat will increase the speed of most enzymatic reactions. Therefore, it is recommended that the test composition be handwarmed for a few minutes prior to the test. A small warming unit or incubator (35°–40° C.) will increase the speed of the reaction in lightly infected specimens.

LIMITATIONS AND WARNINGS

False Positive

Studies indicate that the urease in *proteus, pseudomonas* and *E. coil* is not active in an acid pH where the new test starts. This feature tends to separate out *H. pylori* urease reactivity from others. Patients with complete achlorhydria (pernicious anemia, previous gastric surgery and long term acid suppression by drugs) could have gastric bacterial growth by other urease containing bacteria. In general, these bacteria have less urease and so generally do not produce a rapid positive test.

False Negative

Several factors may produce a false negative result.
a. Patchy Distribution of Infection—the disease has been shown to occur in a patchy distribution so that two antral biopsies are recommended, usually in the immediate prepyloric area and on the lesser curvature of the proximal antrum.
b. Intestinal Metaplasia—*H. pylori* does not colonize intestinal metaplasia so that if this mucosal change is extensive, a false result may occur. Again, multiple biopsies are recommended.
c. Antibiotics—*H. pylori* is sensitive to many antimicrobials including bismuth (Pepto-Bismol). If patients have been on an antimicrobial in the recent past, the organism may be suppressed though usually not eliminated. In this situation, an inadequate number of urease-containing bacteria may be obtained. Females taking short courses of metronidazole for vaginal infections may suppress but not eliminate the bacteria. If recent antibiotics have been used, multiple biopsies should be taken.

In difficult or questionable cases of infection, additional testing by histology, serology or 14C breath test should be considered. The present test composition is intended for in vitro diagnostic use only.

STORAGE: The new test compositions should be stored at 2°–8° C. in the shipping container.

STABILITY: The new test compositions are stable and provide accurate reproducible results for up to 12 months.

In order to more fully explain the invention, the following clinical examples are given.

Clinical Example 1

Patient MAM

This 57 year-old female presented to the office with severe symptoms of dyspepsia and nausea. She had a history of peptic ulcer disease dating back at least 20 years. Endoscopic examination of the stomach and duodenum demonstrated severe peptic ulcers of the stomach and duodenum. Biopsies of the stomach tested by the method of the present invention were positive for the urease containing *Helicobacter pylori* organism. Two blood serologic tests were also positive (Quick-Vue and Omega Lab *H. pylori* Ab Index). The histologic picture subsequently demonstrated active gastritis with identification of the *Helicobacter pylori* organisms. Because the diagnosis was made immediately, appropriate therapy for the infection was begun on the initial office visit.

Example II

Patient KF

This 31 year-old female complained of nausea and vomiting. Endoscopic exam of the upper gastrointestinal tract was performed. A normal examination was observed. Biopsies of the stomach were obtained because it is known that a normal endoscopic examination may still harbor *Helicobacter pylori* organisms and acute gastritis. A test of the present invention was immediately performed with negative results. A diagnosis of non-ulcer dyspepsia was, therefore, made and the patient was treated appropriately with reassurance and acid suppressing drugs. The subsequent histologic exam on other biopsies of the stomach demonstrated normal findings. There was no gastritis or demonstrated normal findings. There was no gastritis or *Helicobacter pylori* organisms found. The result of the test of the prevent invention was, therefore, confirmed.

Example III

Patient AQ

This 44 year-old Indian female was seen because of anemia. A previous stomach operation (gastrojejunostomy) was performed for peptic ulcer disease in 1977. As part of her medical investigation, endoscopic examination of the stomach was performed. The results of the previous surgery were observed but the examination was, otherwise, normal. Since ulcers were previously diagnosed, biopsies for *Helicobacter pylori* were obtained. The standard commercial (CLOtest) urease test and the test of the present invention were both performed. They were both initially negative, but the next morning, the CLOtest test showed a positive result whereas the test of this invention was negative. Subsequent analysis of the histology on the biopsies showed no gastritis and no Helicobacter organisms. Therefore, the present invention test in this instance provided the correct diagnosis whereas the CLOtest test showed a false positive result. Because of these results, no antibiotic therapy was given.

There are several methods presently available to diagnose *H. pylori* gastritis to confirm the quick test results.

a. Culture—The culture of *H. pylori* from biopsy material is difficult and time consuming. It is generally not available in most hospitals or commercial labs.

b. Serology—There are several serologic tests available that measure antibodies against *H. pylori*. The presence of IGG antibody indicates a recent infection. However, it can take six months or more for the antibody level to fall following eradication of the infection (6). So, the presence of antibody does not necessarily indicate the presence of infection.

c. Histology—Routine histologic studies of biopsy material can identify the presence of the bacterium as well as underlying gastritis.

d. 13C or 14C Breath Test—The ingestion of 13C or 14C labeled urea in the presence of *H. pylori* urease results in its intragastric conversion to labeled $CO_2$ which can then be detected in exhaled air. The equipment for this technique is expensive, not widely available and has not yet been approved by the FDA.

BIBLIOGRAPHY

1. Marshall B. J., McGechie D. B., Rogers P. A. R., Glancy R. G. Pyloric Campylobacter infection and gastroduodenal disease. Med J Aust 1985; 149: 439–444.
2. Graham D. Y. *Helicobacter pylori*: Its epidemiology and its role in duodenal ulcer disease. J. Gastroenterol Hepatol 1991; 6:105–13.
3. Parsonnet J., Friedman G. D., Vandersteen D. P., et al: *Helicobacter pylori* infection and the risk of gastric cancer. N Engl J. Med 1991; 325:1127.
4. Hentschel E, Brandstatten G., Dragosics B., et al. Effect of ranitidine and amoxicillin plus metronidazole on the eradication of Helicobacter pylori and the recurrence of duodenal ulcer. N Engl J. Med 1993; 328:308–12.
5. Graham D. Y., Lew G. M., Klein P. D. et al. Effect of treatment of *Helicobacter pylori* infection on the long term recurrence of gastric or duodenal ulcer; a randomized, controlled trial. Ann Intern Med 1992; 116:705–8.
6. Evans D. J., Jr., Graham D. Y., Lew G. M., Evans D. G., Malaty H. M. Can one use the results of serologic testing to monitor the results of therapy of *Helicobacter pylori*? Gastroenterology 1991; 100:A62.
7. Baron C., Thomas T. E., Biochim Biophy Acta; 1975: 382, 276–285.

What is claimed is:

1. In a test composition for the diagnosis of gastric disease by detecting the presence of urease associated with *H. pylori* in a biopsy specimen; said composition containing urea and a dye indicator whereby if *H. pylori* is present in the biopsy specimen the associated urease hydrolyzes the urea to produce ammonia which raises the pH and changes the color of the dye indicator indicating gastric disease;

the improvement which comprises:

said dye indicator comprising at least two dyes in combination which together change color from an initial color to at least one different color indicating the presence of *H. pylori*;

said color change indicating the presence of *H. pylori* initially occurring at an acid pH; and said color indicating the presence of *H. pylori* being distinctive from the color of the biopsy specimen.

2. The composition of claim 1 having an initial pH in the range from about 4.9 to about 5.8 and wherein the color change indicating the presence of *H. pylori* takes place initially below pH 7.0.

3. The composition of claim 2 wherein the dye indicator comprises methyl red and bromthymol blue.

4. The composition of claim 2 wherein the dye indicator changes color with increasing pH over a spectrum of a plurality of colors giving not only an indication of the presence of *H. pylori* but, if present, an indication of the degree of the infection.

5. The composition of claim 1 wherein a positive test indicating the presence of *H. pylori* takes place in most instances in about 2 to about 10 minutes; and in all instances in not more than 4 hours.

6. A test composition for *H. pylori* in the diagnosis of gastric disease, which comprises:

a) about 0.5 to about 2.0% urea;
b) about 0.4 to about 1.4% agar;
c) about 0.2 to about 1.2% N-octyl glucose;
d) about 1.5 mM to about 3.5 mM $NaH_2PO_4$;
e) preservative agent;
f) a dye indicator composition comprising at least two dye indicators in combination which provide a wide spectrum of colors over a wide pH range and indicating a positive result at an acid pH; and
g) water, the remainder;

said composition being in the form of a gel soft enough to easily receive and intimately envelop a biopsy specimen pushed into said gel;

said composition having an initial acid pH;

all percentages being by weight of the total composition.

7. The composition of claim 6 in which the dye indicator composition comprises methyl red and bromthymol blue.

8. The composition of claim 6 in which the preservative agent comprises methyl paraben and propyl paraben.

9. The test composition of claim 6 for *H. pylori* in the diagnosis of gastric disease, which comprises:
a) about 1% urea;
b) about 1% agar;
c) about 1% N-octyl glucose;
d) about 1.5 to about 3.5 mM $NaH_2PO_4$;
e) about 0.2% preservative agent composed of 0.18% methyl paraben and 0.02% propyl paraben;
f) about 25% of a dye indicator containing about 1% methyl red and about 0.1% bromthymol blue;
g) water; the remainder;
said composition being in the form of a gel soft enough to easily receive and intimately envelop a biopsy specimen pushed into said gel;
said composition having an initial pH of about 5.3;
all percentages being by weight of the total composition.

10. The composition of claim 6 which has been sterilized by filtration through a filter having pores of about 0.10 to about 0.5 microns.

* * * * *